(12) United States Patent
Nawracala

(10) Patent No.: US 6,775,002 B2
(45) Date of Patent: Aug. 10, 2004

(54) APPARATUS AND METHOD FOR ABSORBANCE DETECTION

(75) Inventor: Bernd Nawracala, Karlsruhe (DE)

(73) Assignee: Agilent Technologies, Inc., Palo Alto, CA (US)

( * ) Notice: Subject to any disclaimer, the term of this patent is extended or adjusted under 35 U.S.C. 154(b) by 186 days.

(21) Appl. No.: 09/938,232

(22) Filed: Aug. 23, 2001

(65) Prior Publication Data

US 2002/0180974 A1 Dec. 5, 2002

(30) Foreign Application Priority Data

Mar. 28, 2001 (EP) .............................. 01107642

(51) Int. Cl.⁷ .............................................. G01N 21/03
(52) U.S. Cl. ...................................... 356/440; 356/246
(58) Field of Search ......................... 356/246, 433–436, 356/440–442

(56) References Cited

U.S. PATENT DOCUMENTS

| | | | | |
|---|---|---|---|---|
| 3,811,782 A | * | 5/1974 | Kerr | ............................ 356/432 |
| 4,047,819 A | * | 9/1977 | Goldberg | ..................... 356/434 |
| 5,408,326 A | * | 4/1995 | Wang | .......................... 356/410 |
| 6,043,506 A | | 3/2000 | Heffelfinger et al. | ........ 250/584 |
| 6,127,184 A | * | 10/2000 | Wardlaw | ..................... 356/246 |
| 6,154,284 A | * | 11/2000 | McAndrew et al. | ......... 356/437 |
| 6,171,865 B1 | | 1/2001 | Weigl et al. | .................. 436/52 |

FOREIGN PATENT DOCUMENTS

| | | |
|---|---|---|
| EP | 0 458 601 | 11/1991 |
| EP | 0 587 077 | 3/1994 |

* cited by examiner

Primary Examiner—Richard A. Rosenberger

(57) ABSTRACT

An apparatus and method for absorbance detection in instrumental situations which have short absorption path lengths, such as microchip type devices, includes modulating the sample beam incident upon a sample cell to improve the sensitivity of the absorbance measurement. The modulation means includes a scanning device arranged to move the sample beam from a first position in which the sample beam is incident upon the sample area to a second position in which the sample beam is incident upon the cell.

10 Claims, 3 Drawing Sheets

APPARATUS AND METHOD FOR ABSORBANCE DETECTION

BACKGROUND OF THE INVENTION

1. Field of the Invention

The present invention concerns the field of absorbance detection. Specifically, the present invention concerns an apparatus and method for absorbance detection in instrumental situations which have short absorption path lengths. More specifically, the present invention relates to an analytical method and apparatus that employs a lab-on-a-chip device such as electrophoretic or flow injection type microchips.

2. Discussion of the Background Art

Ultraviolet and visible (UV-VIS) absorbance detection provides one of the most general detection methods in spectrochemical analysis. UV-VIS absorbance detection is often used with microchip basal devices. However, these devices inherently offer shallow channel of about 10–20 microns in depth, thus limiting the path length through which the UV-VIS light can travel. This results in a detection sensitivity which is insufficient for such devices to be of practical use.

Several approaches have been tried to overcome the above mentioned limitations. Harrison et al. (Anal. Chem. 1996, 68, 1040–1046) employed a U-cell which increases path length by allowing the beam to pass in a longitudinal direction along the flow channel. However, this cell requires insertion of optical fibers into etched channels making it difficult to manufacture. Harrison (Electrophoresis 2000, 21 1291–1299) also tried a multipath cell in which lithographically fabricated aluminum mirrors above and below the flow channel formed a multireflection cell. A 633 nm Helium Neon laser beam was launched through an aperture into the cell at a slightly angle. This arrangement yielded a 5 to 10 fold increase of effective optical path length. However, this type of device only works with a collimated laser beams. Thus, this approach is unsuited for incoherent lamp light illumination such as is used in UV-VIS absorbance detection methods.

A further method for improving detection sensitivity in microchip devices is disclosed in European patent application EP 0 840 113 A2, which teaches a method and means for simultaneous detection of migration patterns along a channel using cylinder optics to transmit and collect light transmitted through the channel along separation passages, eventually detecting it by means of a photodiode array (PDA) oriented parallel to the channel. The increased integration time improves signal-to-noise ratio, but with the drawback of increased analysis time.

SUMMARY OF THE INVENTION

It is therefore an object of the present invention to provide an apparatus and method for absorbance detection which overcomes the shortcomings as stated above. It is a further object of the present invention to improve the detection limit of UV-VIS absorbance detection in microchip instrumentation.

According to the present invention there is provided an apparatus for measuring absorbance comprising a light source emitting a sample beam which is incident upon a cell having a sample area, the cell being arranged to reflect the sample beam to a detector, characterized in that the apparatus further comprises a modulation means arranged to modulate the sample beam so as to improve the sensitivity of absorbance measurement.

According to an aspect of the present invention, the modulation means includes a scanning device arranged to move the sample beam from a first position in which the sample beam is incident upon said sample area to a second position in which the sample beam is incident upon the cell.

According to a further aspect of the present invention the modulation means may be a linear scanning device. The linear scanning device may be arranged to move the cell. Alternatively, the linear scanning device may be arranged to move an optical element.

In an alternative embodiment of the present invention, the modulation means may be an angular scanning device. The angular scanning device may be a galvanometer.

Advantageously, the present invention increases the analytical sensitivity by doubling optical path length, thus doubling analytical sensitivity, and by reduction of baseline noise by means of modulated or homodyne detection in combination with dual-beam detection for common mode rejection purposes. Doubling of effective optical path length is accomplished by means of reflection type sample light path, while baseline noise reduction is achieved by means of dual-beam detection together with sample modulation and synchronous demodulation. Modulated detection at one certain modulation frequency, also termed homodyne detection, is a proven strategy for recovering small signals buried in asynchronous background and noise. Both homodyne detection, as well as sample modulation, can be implemented with simple circuitry, from example, dual-phase lock-in amplifiers and sample modulation means.

In order to gain the advantages of modulated detection methods, a suitable parameter of measurement needs to be modulated in time periodically with a certain frequency. According to the present invention this is accomplished by a movement of the sample in and out of the sample light path or vice versa using suitable modulation means.

Advantageously, by utilising the back reflection of light launched through the micro channel, the present invention doubles the sensitivity of the apparatus by doubling the absorption path length.

Furthermore, by employing a modulation technique, the baseline noise is reduced, thus further improving the detection limit of the apparatus.

BRIEF DESCRIPTION OF THE DRAWINGS

While the principle advantages and features of the invention have been described above, a greater understanding and appreciation of the invention may be obtained by referring to the drawings and detailed description of the preferred embodiments, presented by way of example only, in which.

DETAILED DESCRIPTION OF THE INVENTION

Figure 1:
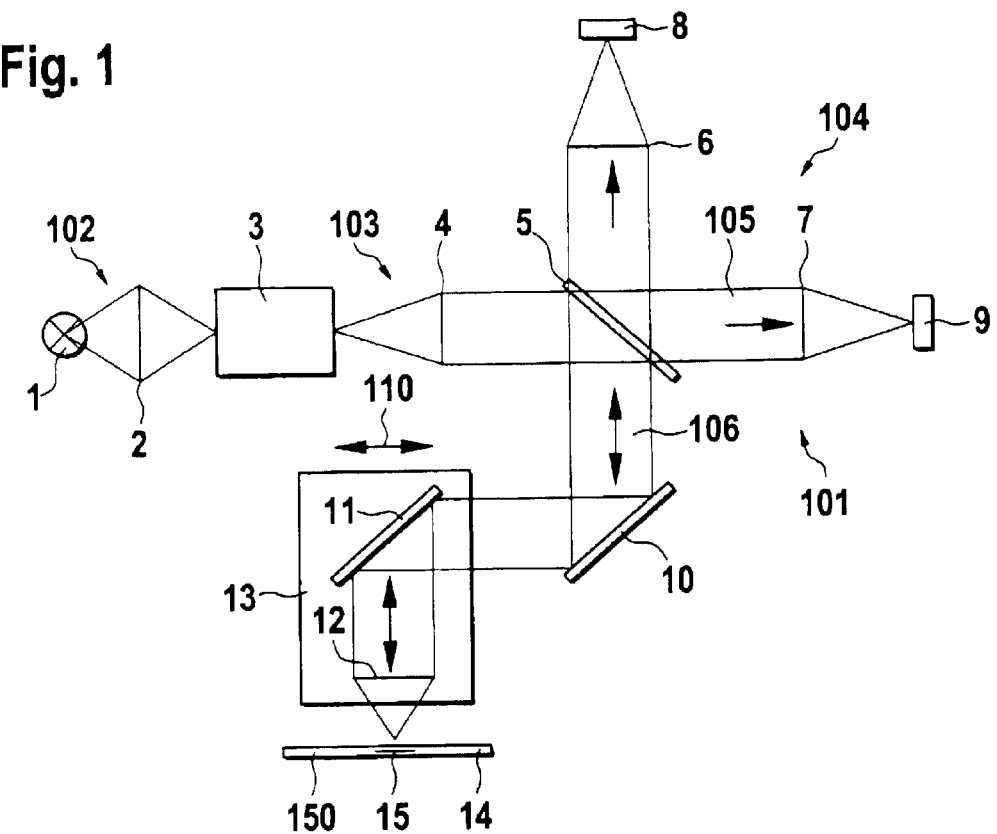
FIG. 1 is a schematic illustration of a first embodiment of the present invention in which sample beam signal modulation is achieved by means of linear translation of the optical element.

In FIG. 1 the optical setup 101 of the first embodiment of the invention is shown. Radiation 102 from light source 1, such as a Deuterium or Tungsten lamp, is launched via optical means 2, such as a lens or mirror, into wavelength selecting device 3, such as a grating, bandpass filter, or monochromator. A monochromatic beam 103 emerges from the wavelength selecting device and is incident upon a double-beam in-space optical configuration 104. The use and operation of double-beam configurations is well known in the art. Monochromatic beam 103 enters the double-beam configuration via additional optical beam steering element 4 and is incident upon semi-transparent mirror 5. A percentage of the monochromatic beam 105 is transmitted by semi-transparent mirror 5 and is incident upon optical steering element 7 which focuses the beam onto reference beam detector 9. Beam 105 is known in the art as the reference beam. A further percentage of the monochromatic beam 106 is reflected by semi-transparent mirror 5 and is incident upon optical steering means 10, preferably a mirror, which then reflects the beam towards movable mirror-lens assembly 13. Beam 106 is known in the art as the sample beam. Assembly 13, which preferable includes a mirror 11 and optical element 12, guides the sample beam through sample area 15 of microchip 14. The sample beam then passes through the sample area and is back-reflected by reflection means 150 disposed within the microchip. The sample beam then returns along the same path through movable mirror-lens assembly 13, optical steering means 10 and again encounters semi-transparent mirror 5. A percentage of the sample beam is transmitted by the semi-transparent mirror and is incident upon optical steering element 6 which focuses the sample beam onto sample beam detector 8.

In FIG. 1 sample beam modulation is achieved by periodically moving back and forth mirror-lens assembly 13 in the directions shown by double arrow 110. This movement causes the sample beam to move from a first position (as shown in FIG. 1) in which the sample beam is passing through sample area 15 to a second position (to the left or right of sample area 15) in which the sample beam is no longer passing through the sample area. However, in both the first and second positions, the sample beam is incident upon reflection means 150, and thus is being back-reflected as described above eventually reaching the sample beam detector 8.

Figure 4:
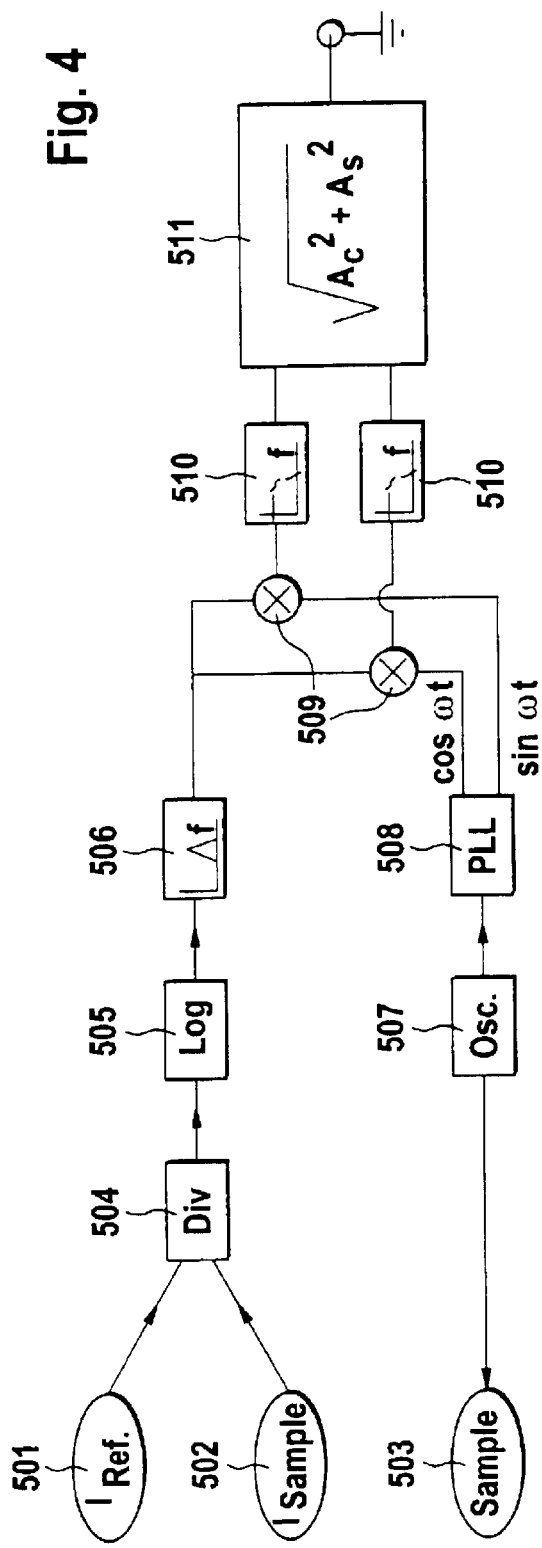
FIG. 4 is a schematic illustration of a dual phase lock-in circuitry used for synchronous detection of the modulated absorbance signal produced by any of the embodiments shown in FIGS. 1–3.

Preferably, the periodic movement of assembly 13 caused by the modulation means is synchronized with detectors 8 and 9. This task is preferably achieved by using a circuit, such as the one shown in FIG. 4, in which a master oscillator 507 supplies the required reference frequency for both the synchronization of the modulation means as well as for generation of sine and cosine signals by means of phase-looked-loop amplifier (PLL) 508 needed for demodulation. The modulated absorbance signal is generated from reference beam signal 501 and sample beam signal 502 by means of divider circuit 504 and logarithm amplifier 505. The absorbance signal is then filtered by bandpass filter 506, whose pass band is centered at modulation frequency ω. By using phase sensitive detectors 509 the absorbance signal components $A_c(t)$ and $A_s(t)$ are generated by means of mixing with the respective sine or cosine signals of PLL amplifier 508. The required absorbance signal A(t) eventually is obtained after rejecting sum frequency 2ω by means of low pass filters 510 and calculation of the signal magnitude by square root circuit 511.

Figure 2:
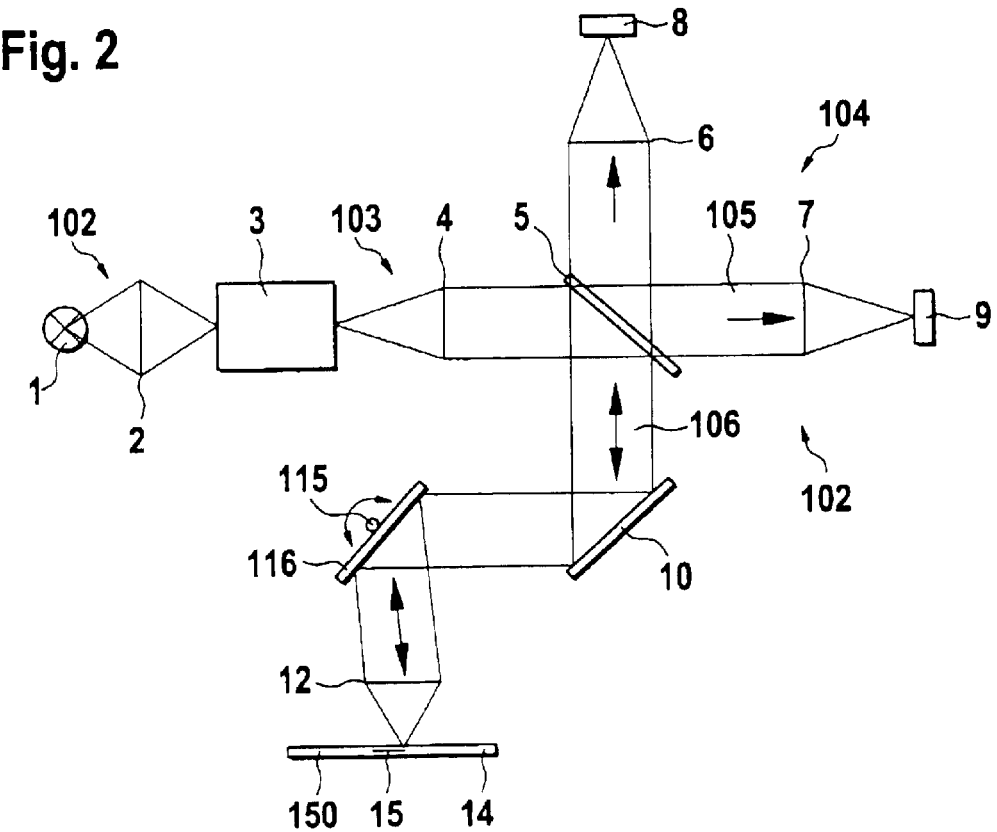
FIG. 2 is a schematic illustration of a second embodiment of the present invention in which sample beam signal modulation is achieved by means of rotation of the optical element.
Figure 3:
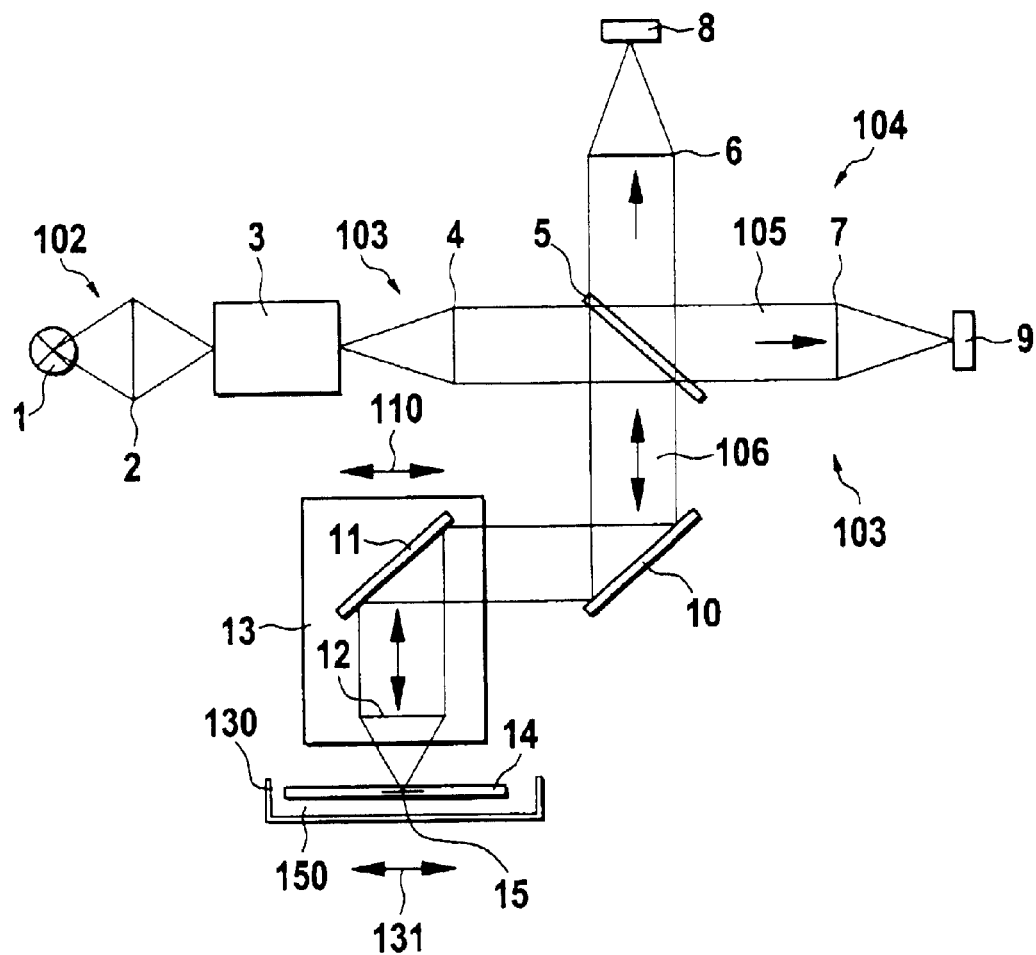
FIG. 3 is a schematic illustration of a third embodiment of the present invention in which sample beam signal modulation is achieved by means of translation of the microchip.

Further embodiments of the present invention in which variations of the modulation means are shown, are given in FIGS. 2 and 3, where parts also appearing in FIG. 1 bear identical numerical designations. In FIG. 2 a similar optical setup 102 as shown in FIG. 1 Is depicted, however here the modulation of the sample beam is realized by varying the angle in which the sample beam is incident upon the microchip. This variation in sample beam angle can be achieved by means of a galvanometer 115 to control the movement of movable scanning mirror 116.

Alternatively, variation of the sample beam angle in order to achieve sample beam scanning may also be achieved by means of holographic, electro-optic, or acousto-optic scanning devices. For these variations, optical element 12 needs to be a flat-field type and produce a sample beam normal to the microchip. Preferably, this can be achieved with a telecentric scan lens or f-theta lens, where the beam displacement is proportional to the scan angle, and the lens is positioned one focal length between the scanner device and the reflector, so that the chief ray of the sample beam is incident normal to the microchip surface.

In figure 3 a similar optical setup 103 as shown in FIGS. 1 and 2 is depicted, however here the modulation of the sample beam is realized by a periodic movement of the microchip below a fixed sample beam. Microchip scanning means 130 is arranged to periodically move the microchip in the directions indicated by double arrow 131. As with the embodiment shown in FIG. 1, the movement of the microchip must be sufficient to move the sample beam from a first position in which the sample beam passes through the sample area 15 to a second position in which the sample beam no longer passed through the sample area.

The periodic movement or wiggling of assembly 13 may be achieved by different modulation means, such as with a linear motor or an electrically actuated piezo device. Preferably, the linear movement of assembly 13 is in the order about 100 microns. However, the amount of movement can be varied according to the degree of modulation required.

The use of any of the embodiments disclosed in FIGS. 1–3 above, advantageously allows for detection of the sample beam as well as the reference beam, thus allowing for common mode rejection of correlated fluctuations, such as light source flicker noise present in both the sample beam and in the reference beam.

Intensity fluctuation present only in the sample beam causes noise in the sample beam signal and thus adversely effects the absorbance signal. Sample modulation decreases the noise when low frequency additive noise is the limiting noise factor. Additive noise is noise which is independent of the analytical signal, such as noise which is present during on- and off-cycle of modulation. The most common sources of additive noise are detector, amplifier, and background signal noise.

In the present invention sample modulation results in a modulated sample beam intensity $I_{S,tot}(\omega, t)$, where ω is a certain modulation frequency. In order to determine the total absorbance $A_{tot}(t)$, the quotient in Eq. 1 has to be calculated as in conventional double-beam absorbance detection from total sample signal $I_{S,tot}$, sample background signal $I_{S,Bg}$, total reference signal $I_{R,tot}$ and reference background signal $I_{R,Bg}$ according to Eq. 1.

$$A_{tot}(t) = \log\left(\frac{I_{R,tot}(t) - I_{R,Bg}}{I_{S,tot}(\omega, t) - I_{S,Bg}}\right) \quad \text{Eq. (1)}$$

The only difference from conventional case is the fact, that $I_{S,tot}(\omega, t)$ is modulated periodically, which is indicated in Eq. (1) above by the modulation frequency parameter $\omega$.

Assuming the modulated total absorbance signal has the form shown in Eq. 2, $$A_{tot}(t) = A_0 + A(t) \cdot \cos(\omega \cdot t + \phi) \quad \text{Eq. (2)}$$

where $A_0$ and $A(t)$ are background and sample absorbance, respectively. The terms $\omega$ and $\phi$ are the modulation frequency and a possible phase shift relative to the phase of the modulation reference frequency. After filtering the absorbance signal at modulation frequency $\omega$ by bandpass filter 506, the absorbance signal is demodulated by two phase sensitive detectors (PSD) 509 by multiplication with the reference signals $\cos(\omega t)$ and $\sin(\omega t)$ according to Eq. 3.

$$A_c(t) = \cos(\omega \cdot t) \cdot A(t) \cdot \cos(\omega \cdot t + \phi)$$

$$A_s(t) = \sin(\omega \cdot t) \cdot A(t) \cdot \cos(\omega \cdot t + \phi) \quad \text{Eq. (3)}$$

The above sine and cosine reference signals are preferably acquired using phase-locked-loop amplifier 508 connected to modulation oscillator 507.

This multiplication shifts the frequency of the modulated absorbance signal, so that the output of the two PSDs 509 are given by Eq. 4.

$$A_c(t) = \frac{1}{2} \cdot A(t) \cdot \cos(2\omega \cdot t + \phi) + \frac{1}{2} \cdot A(t) \cdot \cos(\phi)$$

$$A_s(t) = \frac{1}{2} \cdot A(t) \cdot \sin(2\omega \cdot t + \phi) + \frac{1}{2} \cdot A(t) \cdot \sin(\phi) \quad \text{Eq. (4)}$$

The sum frequency component at $2\omega$ of each PSD output are then rejected by low pass filters 510 and only those frequency components within the low pass filter's narrow bandwidth will pass through For absorbance signals which are in phase with the reference signal, for example $\phi \leq 0$, the value of $A_c(t)$ is equal to $A(t)/2$ and the value of $A_s(t)$ will be zero. In general however, the phase will be non-zero and the absorbance $A(t)$ is given by Eq. 5, $$A(t) = 2 \cdot \sqrt{A_s(t)^2 + A_c(t)^2} \quad \text{Eq. (5)}$$

and is independent of the phase.

The advantage of this modulated detection technique is the fact that by appropriate selection of modulation frequency $\omega$ both signal and signal bandpass may be shifted to a "quiet" part of the noise power density spectrum, for example a spectral region where the integral noise power is lower than around $\omega=0$.

Under detection condition, which is governed by additive non-white noise, such as noise sources showing 1/f noise behaviour like light source flicker noise or resistance fluctuation noise, a reduction results from modulated detection mode so as to allow for recovery of small signals almost completely covered by noise.

Figure 5:
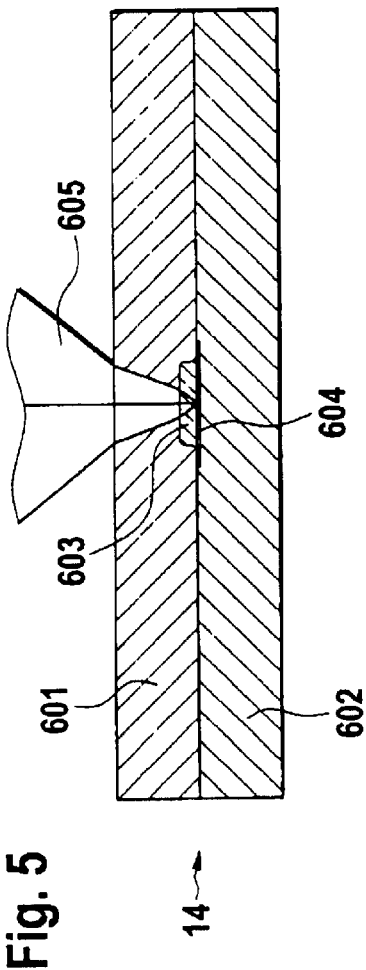
FIG. 5 is a schematic layout of a microchip comprising reflection mean for use in any of the embodiments shown in FIGS. 1–3.

An important aspect of the invention is a dual-path cell microchip comprising suitable reflection means. Preferably the microchip is a sandwiched microchip containing reflection means in direct contact with flow channel detection volume. In FIG. 5 a cross section of one possible embodiment of the microchip 14 shown in FIGS. 1–3 is shown. The glass microchip structure 14 consists of cover-plate 601 and bottom glass plate 603. The coverplate includes microstructured flow channel 603 (not shown to scale) of approximately 60 to 80 microns in width and 10 to 20 microns in depths. The bottom plate includes high reflection means 604 positioned directly opposite the flow channel 603. Reflection means 604 is preferably a photolithographically structured metal coating of high reflectance in the spectral range of use, for example, aluminium or silver coating for UV-VIS applications. During operation the sample beam 605 passes through the flow channel 603 before backreflection by reflection means 604.

As will be appreciated by the skilled person, microstructured chips can be built on various substrates with a range of materials, and with an extensive set of techniques for fabrication of microstructures like channels. For example, glass and quartz chips are of frequent use for lab-on-a-chip devices due to a number of beneficial properties. Besides the advantageous electrical, thermal and optical properties, a large variety of surface modification methods can be easily realized.

The fabrication of channels in glass or quartz chips is usually straightforward and can be achieved with commercially available standard processes. Most commonly, the channel pattern is transferred from a photomask by photolithography to the glass substrate, spin-coated with a thin layer of photosensitive polymer (photoresist) and then exposed to UV light through the photomask. A portion of the photoresist is removed in a developing step, exposing the channel pattern for subsequent etching. The channel is etched using well known etching techniques. The reflection means is then deposited using established thin film deposition methods.

The cover plate and bottom plate are then bonded together, for example, by pressing the plates against each other at about 400° C. for several hours. During this time, atoms diffuse between the substrates forming new chemical bonds between the surfaces.

What is claimed is:

1. Apparatus for measuring absorbance, comprising:
   a light source for emitting a sample beam;
   a modulator for varying a position of incidence of said sample beam upon a cell having a sample area, wherein said modulator includes a scanning device arranged to move said sample beam from a first position in which said sample beam is incident upon said sample area to a second position in which said sample beam is not incident upon said sample area; and
   a detector for detecting a reflection of said sample beam from said cell for an absorbance measurement.

2. Apparatus as claimed in claim 1, wherein said scanning device is a linear scanning device.

3. Apparatus as claimed in claim 2 wherein said linear scanning device is arranged to move said cell.

4. Apparatus as claimed in claim 2, further comprising an optical element upon which said sample beam is incident, wherein said linear scanning device is arranged to move said optical element.

5. Apparatus as claimed in claim 2, wherein said linear scanning device is a motor.

6. Apparatus as claimed in claim 2, wherein said linear scanning device is a piezo-electric device.

7. Apparatus as claimed in claim 1, further comprising an optical element upon which said sample beam is incident, wherein said scanning device is an angular scanning device arranged to move said optical element.

8. Apparatus as claimed in claim 7 wherein said angular scanning device is a galvanometer.

9. Apparatus as claimed in claim 1, wherein said cell comprises a first glass plate bonded to a second glass plate, said first plate having a flow channel formed therein and said second plate having reflection means deposited thereon.

10. Method for measuring absorbance comprising:

transmitting a light beam through a cell having a sample area;

modulating said light beam such that said light beam is moved from a first position in which said light beam is incident upon said sample area to a second position in which said light beam is not incident upon said sample area; and reflecting said light beam from said cell to a detector for an absorbance measurement.

* * * * *